United States Patent
Gebert-Schwarzwaelder et al.

(10) Patent No.: US 10,004,674 B2
(45) Date of Patent: Jun. 26, 2018

(54) SUBSTITUTED P-PHENYLENEDIAMINES AS NEW OXIDATION DYE PRECURSOR PRODUCTS OF THE DEVELOPER TYPE

(71) Applicant: Henkel AG & Co. KGaA, Duesseldorf (DE)

(72) Inventors: Antje Gebert-Schwarzwaelder, Neuss (DE); Helmut Giesa, Meerbusch (DE); Jan-Michael Schoenebeck, Potsdam (DE)

(73) Assignee: Henkel AG & Co. KGaA (DE)

( * ) Notice: Subject to any disclaimer, the term of this patent is extended or adjusted under 35 U.S.C. 154(b) by 0 days. days.

(21) Appl. No.: 15/379,083

(22) Filed: Dec. 14, 2016

(65) Prior Publication Data
US 2017/0165166 A1 Jun. 15, 2017

(30) Foreign Application Priority Data
Dec. 15, 2015 (DE) .................. 10 2015 225 202

(51) Int. Cl.
| | | |
|---|---|---|
| *A61Q 5/10* | (2006.01) | |
| *A61K 8/49* | (2006.01) | |
| *A61K 8/22* | (2006.01) | |
| *A61K 8/34* | (2006.01) | |
| *A61K 8/41* | (2006.01) | |

(52) U.S. Cl.
CPC .............. *A61K 8/4913* (2013.01); *A61K 8/22* (2013.01); *A61K 8/347* (2013.01); *A61K 8/41* (2013.01); *A61K 8/415* (2013.01); *A61K 8/494* (2013.01); *A61Q 5/10* (2013.01); *A61K 2800/4324* (2013.01)

(58) Field of Classification Search
CPC ........ A61Q 5/10; A61K 8/4913; A61K 8/415; A61K 8/347; A61K 8/494; A61K 8/41; A61K 8/22; A61K 2800/4324
See application file for complete search history.

(56) References Cited

U.S. PATENT DOCUMENTS 6,800,097 B2 * 10/2004 Chassot ................. A61K 8/411
544/162

FOREIGN PATENT DOCUMENTS

WO    WO 2007/079800 A1 * 7/2007 .............. A61Q 5/10

OTHER PUBLICATIONS

STIC Search dated Mar. 26, 2017.*
English translation (Apr. 13, 2017) of the Patent No. WO 2007/079800 A1.*
Guilhemat et al., "Fonctionnalisation d'hydrocarbures aromatiques polycycliques. Introduction de fonctions alcool, acide ou amine sur le biphenyle, le fluorene ou le phenanthrene", Bulletin de la Societe Chimique de France, No. 7-8, pp. II-334 to II-344, 1980.

* cited by examiner

*Primary Examiner* — Eisa B Elhilo
(74) *Attorney, Agent, or Firm* — James J. Cummings

(57) ABSTRACT

Compounds, and agents for oxidatively changing the color of keratinic fibers that include such compounds, in particular human hair, in a cosmetic carrier. The compounds are at least one oxidation dye precursor product of formula (I) and/or physiologically acceptable salt thereof,

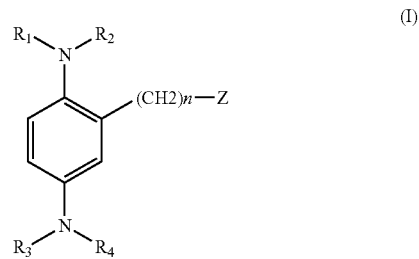

(I)

in which

R1, R2, R3, R4 independently of one another, stand for a hydrogen atom, a $C_1$-$C_6$ alkyl group, a $C_2$-$C_6$ alkenyl group, a hydroxy-($C_1$-$C_6$)-alkyl group, a polyhydroxy-($C_2$-$C_6$)-alkyl group, or a $C_1$-$C_6$-alkoxy-$C_2$-$C_6$-alkyl group, n stands for an integer from 2 to 6, and Z stands for an aromatic or aliphatic heterocycle or for an aromatic or aliphatic carbocycle.

14 Claims, No Drawings

SUBSTITUTED P-PHENYLENEDIAMINES AS NEW OXIDATION DYE PRECURSOR PRODUCTS OF THE DEVELOPER TYPE

FIELD OF THE INVENTION

The present invention generally relates to compounds, and also to agents that include such compounds, for oxidatively changing the color of keratin-containing fibers, in particular human hair.

BACKGROUND OF THE INVENTION

Changing the shape and color of hair is an important field of modern cosmetics. Consumers turn to color-changing agents for the fashionable coloring of hairstyles or to cover grey or even white hair with fashionable or natural color shades.

In order to provide color-changing cosmetic agents, in particular for the skin or keratin-containing fibers, such as human hair, a person skilled in the art is aware of various systems depending on the requirements of the coloration or color change.

What are known as oxidation dyes are used for permanent intense dyes having appropriate fastness properties. Such dyes usually include oxidation dye precursor products, or what are known as developer components and coupler components. The developer components form the actual dyes under the influence of oxidizing agents with coupling to one or more coupler components. The oxidation dyes are characterized by intense, excellent, long-lasting color results.

During the oxidative color change process, developers and couplers diffuse separately into the keratin fibers and form the actual dyes in a chemical reaction with one another under the influence of ammonia as alkalizing agent (or other alkalizing agents such as monoethanolamine) and an oxidizing agent (usually hydrogen peroxide). The developers known from the prior art usually do not form any dyes with one another, or form only very weak, non-specific dyes, and require one or more couplers in order to produce an intense color nuance. The couplers known from the prior art also form only weak dyes with one another and must be made to react with at least one developer in order to attain an intense, bright color result.

In spite of their advantageous coloring properties, oxidative hair dyes are associated with various disadvantages for the user. In particular, it is suspected for some of the conventional oxidation dye precursor products, including p-phenylenediamine itself, that these have an irritating or aggravating effect for some users and thus trigger sensitizations or even allergic reactions. For these substances, there is thus a need for further improvement in respect of their physiological compatibility profile. Many compounds have been researched in the quest for replacement substances, however these are often afflicted by use-related problems, such as insufficient fastness properties. In addition, in spite of already highly developed dyeing systems, there is also a need for dyeing systems with which excellent brightness and intensity of the dyeing results can be attained and which at the same time have very good durability and excellent homogeneity.

It is therefore desirable to reduce the above-mentioned disadvantages of oxidative hair dyes. Dyes should produce intense colorings with high colorfulness and with good resistance to external influences, in particular with good fastness to light and washing, which also do not experience any color fading or color change, even once the hair has been shampooed multiple times. In addition, the dyes should have excellent leveling capacity to the greatest possible extent and should be less selective, i.e. they should result in uniform, consistent color results to the greatest possible extent on hair that has been pre-treated to varying degrees. In addition, the dyes should have an advantageous profile in terms of toxicology.

Furthermore, other desirable features and characteristics of the present invention will become apparent from the subsequent detailed description of the invention and the appended claims, taken in conjunction with this background of the invention.

BRIEF SUMMARY OF THE INVENTION

An agent for oxidatively changing the color of keratinic fibers, in particular human hair, includes, in a cosmetic carrier, at least one oxidation dye precursor product of formula (I) and/or physiologically acceptable salt thereof,

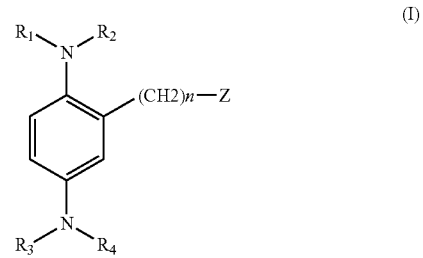

in which R1, R2, R3, R4 independently of one another, stand for a hydrogen atom, a $C_1$-$C_6$ alkyl group, a $C_2$-$C_6$ alkenyl group, a hydroxy-($C_1$-$C_6$)-alkyl group, a polyhydroxy-($C_2$-$C_6$)-alkyl group, or a $C_1$-$C_6$-alkoxy-$C_2$-$C_6$-alkyl group; n stands for an integer from 2 to 6; and Z stands for an aromatic or aliphatic heterocycle or for an aromatic or aliphatic carbocycle.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now been found that certain p-phenylenediamine derivatives, which in the 2-position of their phenyl ring are linked via an alkylene unit to a cyclic grouping, are particularly well suited as oxidation dye precursors for dyeing keratin-containing fibers. These new oxidation dye precursor products result in colorations that have a high color intensity and excellent brightness alongside good fastness properties as well.

A first subject of the present invention is an agent for oxidatively changing the color of keratinic fibers, in particular human hair, including, in a cosmetic carrier, at least one oxidation dye precursor product of formula (I) and/or physiologically acceptable salt thereof,

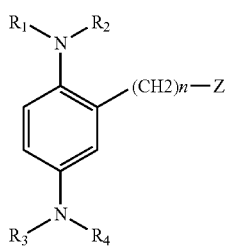

(I)

in which
R1, R2, R3, R4 independently of one another, stand for a hydrogen atom, a $C_1$-$C_6$ alkyl group, a $C_2$-$C_6$ alkenyl group, a hydroxy-($C_1$-$C_6$)-alkyl group, a polyhydroxy-($C_2$-$C_6$)-alkyl group, or a $C_1$-$C_6$-alkoxy-$C_2$-$C_6$-alkyl group, n stands for an integer from 2 to 6, and Z stands for an aromatic or aliphatic heterocycle or for an aromatic or aliphatic carbocycle.

Keratinic fibers are understood to mean wool, furs, feathers and in particular human hair. The dyes according to the invention, however, can also be used in principle for the dyeing of other natural fibers, such as cotton, jute, sisal, canvas or silk, modified natural fibers such as regenerated cellulose, nitro cellulose, alkyl cellulose or hydroxyalkyl cellulose or acetyl cellulose. The oxidative color changing of human hair, which is performed at a temperature of at most 40° C., is explicitly very particularly preferred.

The agents according to the invention include the oxidation dye precursor products of formula (I) in a cosmetic carrier, preferably in a suitable aqueous, alcoholic, or aqueous-alcoholic carrier. For the purposes of hair dyeing, such carriers are, for example, creams, emulsions, gels, or also surfactant-containing foaming solutions, such as shampoos, foam aerosols, foam formulations, or other preparations suitable for application to the hair. It is also conceivable, however, to integrate the dye precursor products according to formula (I) in a powdery or also tablet-like formulation.

In the sense of the present invention, aqueous-alcoholic solutions are understood to mean aqueous solutions that include 3 to 70% by weight of a $C_1$-$C_4$ alcohol, in particular ethanol or isopropanol. The agents according to the invention can additionally include further organic solvents, such as methoxybutanol, benzyl alcohol, ethyldiglycol, or 1,2-propylene glycol. All water-soluble organic solvents are preferred here.

The term "agents for oxidatively changing the color" used in accordance with the invention is understood to mean oxidative dyes which include at least one oxidation dye precursor product of formula (I). The coloring can be formed by the presence of atmospheric oxygen, but preferably by the presence of an oxidizing agent different from atmospheric oxygen. In the latter case, the oxidizing agent is generally hydrogen peroxide. Depending on the amount of oxidizing agent used, the keratin fibers are lightened simultaneously to a greater or lesser extent during the dyeing, since the oxidizing agent initiates not only the dye forming process of developers and couplers, but also oxidatively destroys the hair's inherent pigments (melanins).

Depending on the used amounts of the oxidation dye precursor products and of the oxidizing agent, the oxidative color change can therefore be predominantly a coloration (with high dye proportion) or predominantly a lightening (with high proportion of oxidizing agent). In the latter case the oxidation dye precursor products are used primarily to provide some shading to the result of the lightening process.

The agents according to the invention for oxidatively changing the color of keratinic fibers include, as an ingredient essential to the invention, at least one oxidation dye precursor product of formula (I). Examples for the substituents R1, R2, R3, R4, R5 and Z specified in formula (I) will be specified by way of example hereinafter:

A hydroxy group means an —OH group. Examples of $C_1$-$C_6$ alkyl groups are —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, —(CH$_2$)$_4$CH$_3$, —(CH$_2$)$_5$CH$_3$. Particularly preferred alkyl groups are methyl and ethyl. Examples of $C_2$-$C_6$ alkenyl groups are prop-2-enyl (allyl group), 2-methyl-prop-2-enyl, but-3-enyl, but-2-enyl, pent-4-enyl or pent-3-enyl. Examples of $C_1$-$C_6$ hydroxyalkyl groups are —CH$_2$OH, —CH$_2$CH$_2$OH, —CH$_2$CH$_2$CH$_2$OH, —CH$_2$CH(OH)CH$_3$, —CH$_2$CH$_2$CH$_2$CH$_2$OH, wherein —CH$_2$CH$_2$OH is preferred. Examples of $C_2$-$C_6$ polyhydroxyalkyl groups are 2,3-dihydroxypropyl group, 3,4-dihydroxybutyl group, 2,4-dihydroxybutyl group, and 1,2 dihydroxyethyl group. Examples of $C_1$-$C_6$ alkoxy groups are —OCH$_3$, —OCH$_2$CH$_3$, —OCH$_2$CH$_2$CH$_3$, —OCH(CH$_3$)$_2$ or —OC(CH$_3$)$_3$, with the methoxy group (—OCH$_3$) being preferred. An amino group means an —NH2 group. examples of a $C_1$-$C_6$ alkoxy-$C_2$-$C_6$ alkyl group are the 2-(methoxy)ethyl group, the 3-(methoxy)propyl group, the 2-(ethoxy)ethyl group, and the 3-(ethoxy)propyl group.

In the compounds of formula (I) the groups R1, R2, R3 and R4, independently of one another, stand for a hydrogen atom, a $C_1$-$C_6$ alkyl group, a $C_2$-$C_6$ alkenyl group, a hydroxy-($C_1$-$C_6$)-alkyl group, a polyhydroxy-($C_2$-$C_6$)-alkyl group or a $C_1$-$C_6$-alkoxy-$C_2$-$C_6$-alkyl group.

By means of the selection of suitable substituents R1 to R4, the substantivity of the compounds on the hair is optimized, and their shading result can also be modified.

Furthermore, with the synthesis of the compounds of formula (I) by the selection of suitable substituents R1 to R4, the purification and the yield of the compounds can be improved.

In this context it is preferable when the groups R1, R2, R3 and R4 in the compounds of formula (I), independently of one another, stand for a hydrogen atom, a $C_1$-$C_6$ alkyl group, or a 2-(hydroxy)ethyl group.

In a preferred embodiment an agent according to the invention is therefore characterized in that it includes at least one oxidation dye precursor product in which
R1, R2, R3, R4 independently of one another, stand for a hydrogen atom, a $C_1$-$C_6$ alkyl group or a 2-(hydroxy)ethyl group (i.e. an HO—CH$_2$—CH$_2$ group).

Furthermore, it has proven to be advantageous when oxidation dye precursor products of formula (I) are used in which one of the groups from R1, R2, R3 and R4 stands for a $C_1$-$C_6$ alkyl group, preferably for a methyl group, and the other three groups from R1, R2, R3 and R4 stand for a hydrogen atom. By way of example, it is thus particularly preferred when
  the group R1 stands for a methyl group and the three groups R2, R3 and R4 stand for a hydrogen atom, or
  the group R3 stands for a methyl group and the three groups R1, R2 and R4 stand for a hydrogen atom, or
  the group R1 stands for an ethyl group and the three groups R2, R3 and R4 stand for a hydrogen atom, or
  the group R3 stands for an ethyl group and the three groups R1, R2 and R4 stand for a hydrogen atom.

In a further preferred embodiment an agent according to the invention is therefore characterized in that it includes at least one oxidation dye precursor product of formula (I) in which one of the groups from R1, R2, R3 and R4 stands for a $C_1$-$C_6$ alkyl group, preferably for a methyl group, and the other three groups from R1, R2, R3 and R4 stand for a hydrogen atom.

When the groups R3 and R4 in the compounds of formula (I) both stand for a hydrogen atom, colorings with particularly clear shades can also be attained. It is therefore also very particularly preferred when the groups R3 and R4 both stand for a hydrogen atom.

In a further preferred embodiment an agent according to the invention is characterized in that it includes at least one oxidation dye precursor product of formula (I) in which R3 and R4 both stand for a hydrogen atom.

The group R1 in the compounds of formula (I) also particularly preferably stands for a $C_1$-$C_6$ alkyl group, very particularly preferably for a methyl group, or for a hydrogen atom, and the group R2 stands for a hydrogen atom.

In a further preferred embodiment an agent according to the invention is characterized in that it includes at least one oxidation dye precursor product of formula (I) in which R1 stands for a methyl group or for a hydrogen atom, and R2 stands for a hydrogen atom.

The number n in the compounds of formula (I) specifies the length of the alkylene chain —$(CH_2)_n$—. Here, n can stand for an integer from 2 to 6.

The suitable choice of the number n also influences the intensity of the colorings. The intense color results can be attained with the compounds of formula (I) in which n stands for the number 2 or 3, very particularly for the number 2.

In a further preferred embodiment an agent according to the invention is characterized in that it includes at least one oxidation dye precursor product of formula (I) in which
n stands for an integer from 2 to 3, preferably for the number 2.

A very particularly preferred embodiment of the present invention is therefore an agent for oxidatively changing the color of keratinic fibers, in particular human hair, including, in a cosmetic carrier, at least one oxidation dye precursor product of formula (I) and/or physiologically acceptable salt thereof,

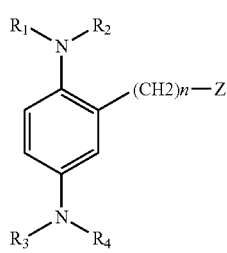

(I)

in which
R1 stands for a methyl group or for a hydrogen atom,
R2, R3 and R4 stand for a hydrogen atom,
n stands for the number 2,
Z stands for an aromatic or aliphatic heterocycle or for an aromatic or aliphatic carbocycle.

The grouping Z stands for an aromatic or aliphatic heterocycle or for an aromatic or aliphatic carbocycle. The grouping Z is uncharged in accordance with the invention.

An aromatic heterocycle is understood in accordance with the invention to mean an aromatic, preferably 5- or 6-membered ring, which includes at least one heteroatom, preferably oxygen, sulfur, or nitrogen.

Examples of aromatic heterocycles according to the invention are a pyridin-2-yl ring, a pyridin-3-yl ring, a pyridin-4-yl ring, a 1H-imidazol-1-yl ring, a 1H-imidazol-2-yl ring, a 1H-pyrrol-1-yl ring, a 1H-pyrrol-2-yl ring, a thiazol-2-yl ring, a thiazol-4-yl ring, a thiazol-5-yl ring, an oxazol-2-yl ring, an oxazol-4-yl ring or an oxazol-5-yl ring.

An aliphatic heterocycle is understood in accordance with the invention to mean an aliphatic, i.e. not aromatic, saturated or unsaturated, preferably 5-, 6- or 7-membered ring, which includes at least one heteroatom, preferably oxygen, sulfur, or nitrogen.

Examples of aliphatic heterocycles according to the invention include a piperidin-1-yl ring, a pyrrolidin-1-yl ring, a morpholin-4-yl ring, a piperazin-1-yl ring or a thiomorpholin-4-yl ring. Here, the piperazin-1-yl ring optionally can also be substituted at the second nitrogen atom located in the 4-position.

Particularly intense color shades could be obtained with compounds of formula (I) in which the grouping Z stands for an aromatic or aliphatic heterocycle.

In a further preferred embodiment an agent according to the invention is characterized in that it includes at least one oxidation dye precursor product of formula (I) in which
Z stands for an aromatic or aliphatic heterocycle of formulas (II) to (X),

(II)

(III)

(IV)

(V)

(VI)

(VII)

(VIII)

(IX)

(X)

in which

R5 stands for a hydrogen atom, a $C_1$-$C_6$ alkyl group, or a $C_2$-$C_6$ alkenyl group.

The heterocycle of formula (II) is a pyrrolidin-1-yl group.
The heterocycle of formula (III) is a piperidin-1-yl group.
The heterocycle of formula (IV) is a porpholin-4-yl group.
The heterocycle of formula (V) is a 1H-pyrrol-1-yl group.
The heterocycle of formula (VI) is a 1H-pyrazol-1-yl group.
The heterocycle of formula (VI) is a 1H-imidzazol-1-yl group.
The heterocycle of formula (VIII) is a piperazin-1-yl group which is substituted in the 4-position by the group R5.
The heterocycle of formula (IX) is a thiomorpholin-4-yl group.
The heterocycle of formula (X) is a 2,5-dihydro-1H-pyrrol-1-yl group.

In the formula schemas of compounds (II) to (X), the wavy line specifies the connection point between the grouping Z and the alkylene unit —$(CH_2)_n$—. In the case of a compound of formula (I) in which R1 to R4 stand for hydrogen atoms, n stands for the number 2 and Z stands for the formula (II), the compound is therefore the compound 2-[2-(pyrrolidin-1-yl)ethyl]benzene-1,4-diamine

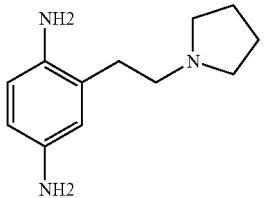 [SMILES: Nc1ccc(N)c(CCN2CCCC2)c1]

In this context, it is very particularly preferred when the grouping Z in the compounds of formula (I) stands for an aromatic or aliphatic heterocycle of formula (II), (III), (IV) or (V). It is most generally preferred when the grouping Z stands for the formula (II).

In a further particularly preferred embodiment, an agent according to the invention is characterized in that it includes at least one oxidation dye precursor product of formula (I) in which Z stands for an aromatic or aliphatic heterocycle of formula (II), (III), (IV) or (V)

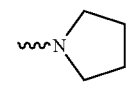
(II)

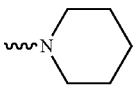
(III)

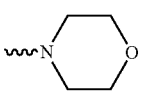
(IV)

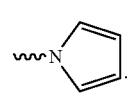
(V)

In yet a further preferred embodiment, an agent according to the invention is characterized in that it includes at least one oxidation dye precursor product of formula (I) in which Z stands for an aliphatic heterocycle of formula (II), (III) or (IV)

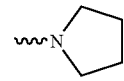
(II)

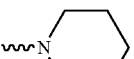
(III)

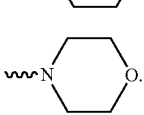
(IV)

In an explicitly very particularly preferred embodiment, an agent according to the invention is characterized in that it includes at least one oxidation dye precursor product of formula (I) in which Z stands for an aromatic or aliphatic heterocycle of formula (II)

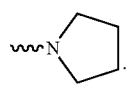
(II)

A further very particularly preferred embodiment of the present invention is therefore an agent for oxidatively changing the color of keratinic fibers, in particular human hair, including, in a cosmetic carrier, at least one oxidation dye precursor product of formula (I) and/or physiologically acceptable salt thereof,

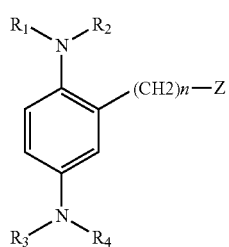
(I)

in which

R1 stands for a methyl group or for a hydrogen atom,
R2, R3 and R4 stand for a hydrogen atom,
n stands for the number 2,
Z stands for an aliphatic heterocycle of formula (II), (III) or (IV)

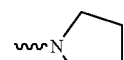
(II)

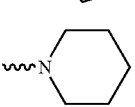
(III)

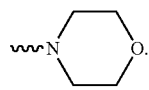 (IV)

Furthermore, the grouping Z in the compounds of formula (I) can also stand for an aromatic or aliphatic carbocycle.

An aromatic carbocycle is understood in accordance with the invention to be a phenyl group in particular. An aliphatic carbocycle is understood in accordance with the invention to be a carbocyclic, not aromatic, saturated or unsaturated, preferably 5- or 6-membered ring. Examples of an aliphatic carbocycle include the cyclohexyl group and the cyclopentyl group.

In a further embodiment an agent according to the invention is characterized in that it includes at least one oxidation dye precursor product of formula (I) in which
Z stands for an aromatic or aliphatic carbocycle of formulas (XI) to (XIII)

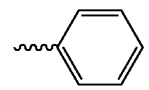 (XI)

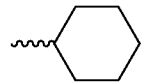 (XII)

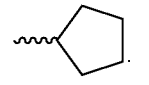 (XIII)

In a further preferred embodiment an agent according to the invention is characterized in that it includes at least one oxidation dye precursor product of formula (I) from the group formed from
1-N-methyl-2-[2-(pyrrolidin-1-yl)ethyl]benzene-1,4-diamine

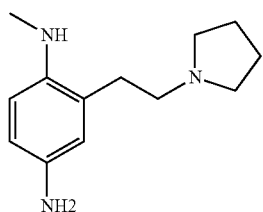 [SMILES: CNc1ccc(N)cc1CCN1CCCC1]

1-N-methyl-2-[2-(piperidin-1-yl)ethyl]benzene-1,4-diamine

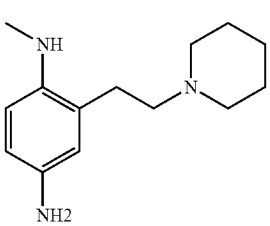 [SMILES: CNc1ccc(N)cc1CCN1CCCCC1]

1-N-methyl-2-[2-(morpholin-4-yl)ethyl]benzene-1,4-diamine

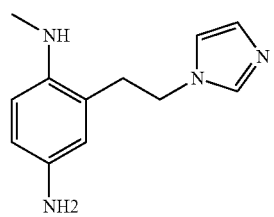 [SMILES: CNc1ccc(N)cc1CCn1ccnc1]

1-N-methyl-2-[2-(1H-pyrrol-1-yl)ethyl]benzene-1,4-diamine

1-N-methyl-2-[2-(1H-pyrazol-1-yl)ethyl]benzene-1,4-diamine

1-N-methyl-2-[2-(1H-imidazol-1-yl)ethyl]benzene-1,4-diamine

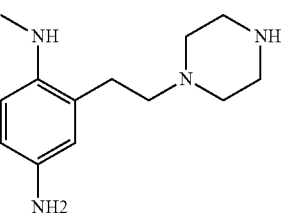 [SMILES: CNc1ccc(N)cc1CCN1CCNCC1]

1-N-methyl-2-[2-(piperazin-1-yl)ethyl]benzene-1,4-diamine

1-N-methyl-2-[2-(4-methylpiperazin-1-yl)ethyl]benzene-1,4-diamine

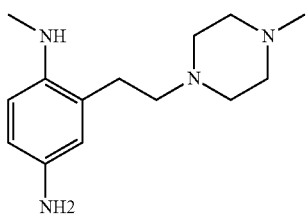 [SMILES: CNc1ccc(N)cc1CCN1CCN(C)CC1]

1-N-methyl-2-[2-(thiomorpholin-4-yl)ethyl]benzene-1,4-diamine

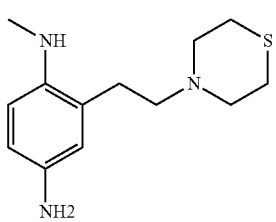 [SMILES: CNc1ccc(N)cc1CCN1CCSCC1]

1-N-methyl-2-[2-(2,5-dihydro-1H-pyrrol-1-yl)ethyl]benzene-1,4-diamine

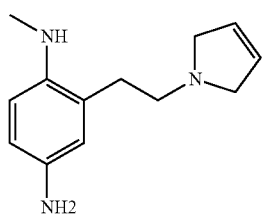 [SMILES: CNc1ccc(N)cc1CCN1CC=CC1]

1-N-methyl-2-[3-(pyrrolidin-1-yl)propyl]benzene-1,4-diamine

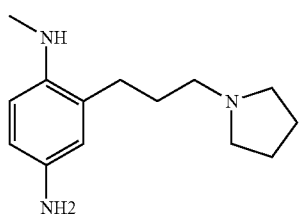 [SMILES: CNc1ccc(N)cc1CCCN1CCCC1]

1-N-methyl-2-[3-(piperidin-1-yl)propyl]benzene-1,4-diamine

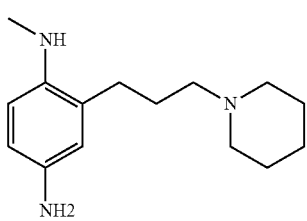 [SMILES: CNc1ccc(N)cc1CCCN1CCCCC1]

1-N-methyl-2-[3-(morpholin-4-yl)propyl]benzene-1,4-diamine

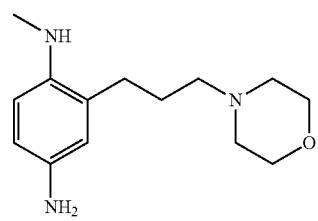

1-N-methyl-2-[3-(1H-pyrrol-1-yl)propyl]benzene-1,4-diamine

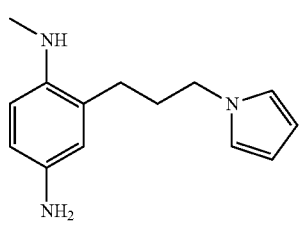 [SMILES: CNc1ccc(N)cc1CCCn1cccc1]

1-N-methyl-2-[3-(1H-pyrazol-1-yl)propyl]benzene-1,4-diamine

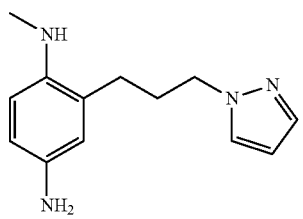 [SMILES: CNc1ccc(N)cc1CCCn1cccn1]

1-N-methyl-2-[3-(1H-imidazol-1-yl)propyl]benzene-1,4-diamine

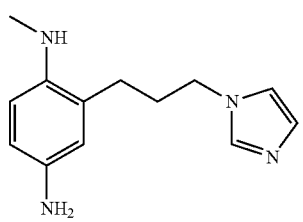 [SMILES: CNc1ccc(N)cc1CCCn1ccnc1]

1-N-methyl-2-[3-(piperazin-1-yl)propyl]benzene-1,4-diamine

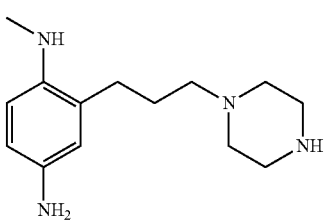 [SMILES: CNc1ccc(N)cc1CCCN1CCNCC1]

1-N-methyl-2-[3-(4-methylpiperazin-1-yl)propyl]benzene-1,4-diamine

13
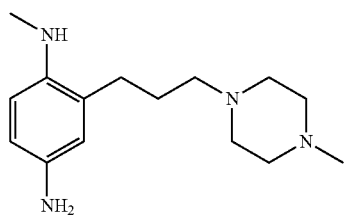 [SMILES: CNc1ccc(N)cc1CCCN1CCN(C)CC1]
1-N-methyl-2-[3-(thiomorpholin-4-yl)propyl]benzene-1,4-diamine
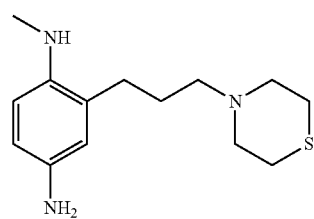 [SMILES: CNc1ccc(N)cc1CCCN1CCSCC1]
1-N-methyl-2-[3-(2,5-dihydro-1H-pyrrol-1-yl)propyl]benzene-1,4-diamine
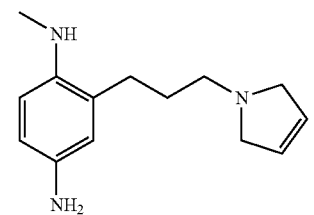 [SMILES: CNc1ccc(N)cc1CCCN1CC=CC1]
2-[2-(pyrrolidin-1-yl)ethyl]benzene-1,4-diamine
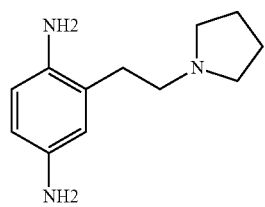 [SMILES: Nc1ccc(N)c(CCN2CCCC2)c1]
2-[2-(piperidin-1-yl)ethyl]benzene-1,4-diamine
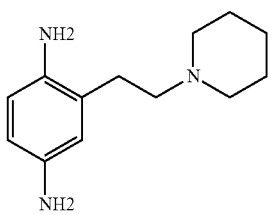 [SMILES: Nc1ccc(N)c(CCN2CCCCC2)c1]
14
2-[2-(morpholin-4-yl)ethyl]benzene-1,4-diamine
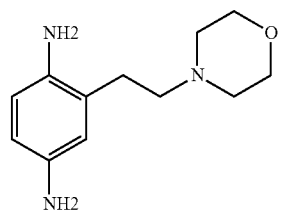 [SMILES: Nc1ccc(N)c(CCN2CCOCC2)c1]
2-[2-(1H-pyrrol-1-yl)ethyl]benzene-1,4-diamine
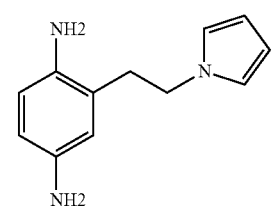 [SMILES: Nc1ccc(N)c(CCn2cccc2)c1]
2-[2-(1H-pyrazol-1-yl)ethyl]benzene-1,4-diamine
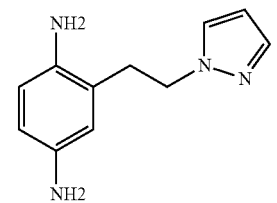 [SMILES: Nc1ccc(N)c(CCn2cccn2)c1]
2-[2-(1H-imidazol-1-yl)ethyl]benzene-1,4-diamine
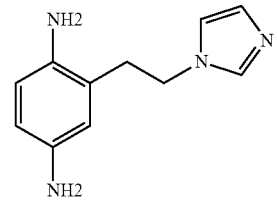 [SMILES: Nc1ccc(N)c(CCn2ccnc2)c1]
2-[2-(piperazin-1-yl)ethyl]benzene-1,4-diamine
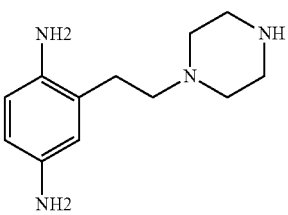 [SMILES: Nc1ccc(N)c(CCN2CCNCC2)c1]

2-[2-(4-methylpiperazin-1-yl)ethyl]benzene-1,4-diamine

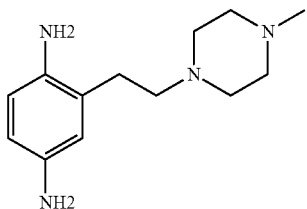 [SMILES: CN1CCN(CCc2cc(N)ccc2N)CC1]

2-[2-(thiomorpholin-4-yl)ethyl]benzene-1,4-diamine

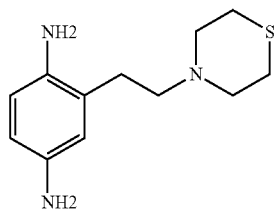 [SMILES: Nc1ccc(N)c(CCN2CCSCC2)c1]

2-[2-(2,5-dihydro-1H-pyrrol-1-yl)ethyl]benzene-1,4-diamine

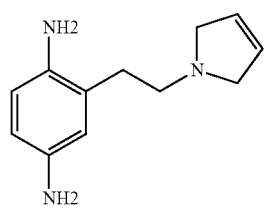 [SMILES: Nc1ccc(N)c(CCN2CC=CC2)c1]

2-[3-(pyrrolidin-1-yl)propyl]benzene-1,4-diamine

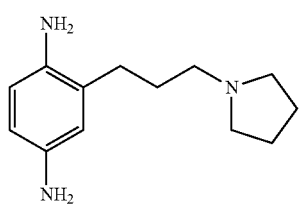 [SMILES: Nc1ccc(N)c(CCCN2CCCC2)c1]

2-[3-(piperidin-1-yl)propyl]benzene-1,4-diamine

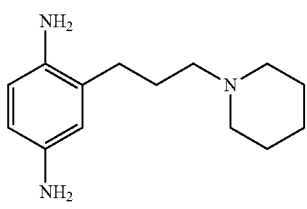 [SMILES: Nc1ccc(N)c(CCCN2CCCCC2)c1]

2-[3-(morpholin-4-yl)propyl]benzene-1,4-diamine

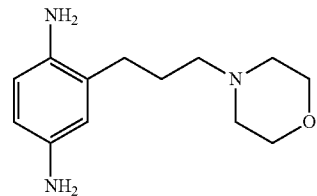 [SMILES: Nc1ccc(N)c(CCCN2CCOCC2)c1]

2-[3-(1H-pyrrol-1-yl)propyl]benzene-1,4-diamine

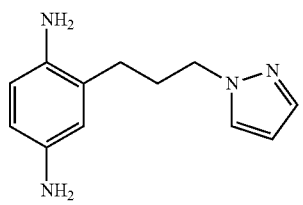 [SMILES: Nc1ccc(N)c(CCCn2cccn2)c1]

2-[3-(1H-pyrazol-1-yl)propyl]benzene-1,4-diamine

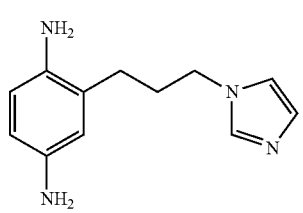 [SMILES: Nc1ccc(N)c(CCCn2ccnc2)c1]

2-[3-(1H-imidazol-1-yl)propyl]benzene-1,4-diamine

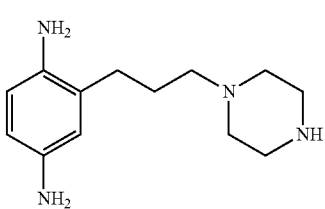 [SMILES: Nc1ccc(N)c(CCCN2CCNCC2)c1]

2-[3-(piperazin-1-yl)propyl]benzene-1,4-diamine

2-[3-(4-methylpiperazin-1-yl)propyl]benzene-1,4-diamine

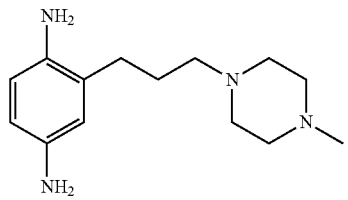 [SMILES: CN1CCN(CCCc2cc(N)ccc2N)CC1]

2-[3-(thiomorpholin-4-yl)propyl]benzene-1,4-diamine

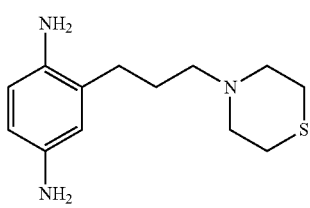 [SMILES: Nc1ccc(N)c(CCCN2CCSCC2)c1]

2-[3-(2,5-dihydro-1H-pyrrol-1-yl)propyl]benzene-1,4-diamine

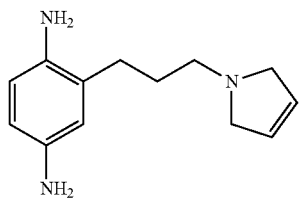 [SMILES: Nc1ccc(N)c(CCCN2CC=CC2)c1]

and/or the physiologically acceptable salts of these compounds.

Within the aforementioned group, the following compounds have a very particularly good coloring capability. The use of one or more oxidation dyes of formula (I) from the following group—and/or the physiologically acceptable salts hereof—is therefore explicitly very particularly preferred:

1-N-methyl-2-[2-(pyrrolidin-1-yl)ethyl]benzene-1,4-diamine

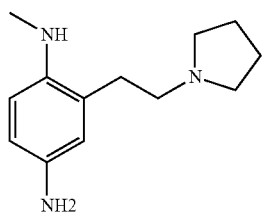 [SMILES: CNc1ccc(N)cc1CCN1CCCC1]

1-N-methyl-2-[2-(piperidin-1-yl)ethyl]benzene-1,4-diamine

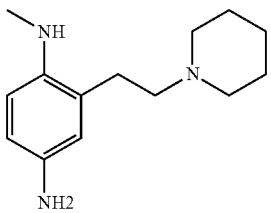 [SMILES: CNc1ccc(N)cc1CCN1CCCCC1]

1-N-methyl-2-[2-(morpholin-4-yl)ethyl]benzene-1,4-diamine

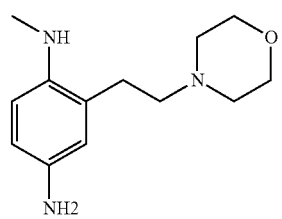 [SMILES: CNc1ccc(N)cc1CCN1CCOCC1]

2-[2-(pyrrolidin-1-yl)ethyl]benzene-1,4-diamine

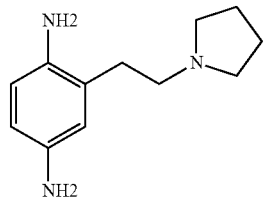 [SMILES: Nc1ccc(N)c(CCN2CCCC2)c1]

2-[2-(piperidin-1-yl)ethyl]benzene-1,4-diamine

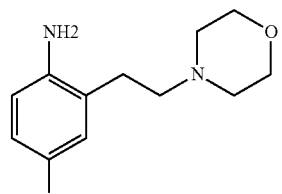

2-[2-(morpholin-4-yl)ethyl]benzene-1,4-diamine

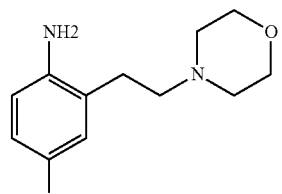

and/or the physiologically acceptable salts of these compounds.

The oxidation dye precursor products of formula (I) according to the invention are amino compounds which can also be used in the form of their physiologically acceptable salts. A physiologically acceptable salt of a compound of formula (I) is understood to be a salt which, compared to its free compound, can be applied to the hair and scalp of a person without toxicological disadvantages.

Physiologically acceptable salts in the sense of this invention are in particular the chlorides, the sulfates, and the bromides. Further preferred physiologically acceptable salts are derived from sulfonic acids, such as benzene sulfonates, p-toluenesulfonyl sulfonates, $C_1$-$C_4$ alkane sulfonates or trifluoromethane sulfonates. Depending on the number of amino groups included in the compounds according to the invention, mono-, di-, tri-, tetra- and higher adducts can be present as salts.

The physiologically acceptable salts of oxidation dye precursor products of formula (I) mean, in particular, the hydrochlorides, the hydrobromides, and the sulfates of these compounds.

The oxidation dye precursor product(s) of formula (I) can be included in the agents according to the invention in a total amount of from 0.001 to 5.0% by weight, preferably from 0.001 to 5.0% by weight, preferably from 0.05 to 4.5% by weight, more preferably from 0.1 to 4.0% by weight, and particularly preferably from 0.15 to 3.5% by weight, in relation to the total weight of the agent.

The used amount of the compounds of formula (I) will be selected by a person skilled in the art depending on the desired color shade and color depth.

In a further embodiment an agent according to the invention is characterized in that it includes one or more oxidation dye precursor products of formula (I) in a total amount of from 0.001 to 5.0% by weight, preferably from 0.05 to 4.5% by weight, more preferably from 0.1 to 4.0% by weight, and particularly preferably from 0.15 to 3.5% by weight, in relation to the total weight of the agent.

The compounds of formula (I) are oxidation dye precursor products of the developer type. The compounds of formula (I) can be included in principle as the sole color-changing compounds in the agent according to the invention. It is preferred in accordance with the invention, however, when the agent additionally includes at least one oxidation dye precursor product of the coupler component type.

Coupler components alone do not provide significant coloring within the scope of oxidative coloring, but instead always require the presence of developer components. Coupler components in the sense of the invention allow at least one substitution of a chemical group of the coupler by the oxidized form of the developer component. Here, covalent bonds form between the coupler and developer components.

At least one compound from one of the following classes is preferably selected as coupler component suitable in accordance with the invention:
  m-aminophenol and/or derivatives thereof,
  m-diaminobenzene and/or derivatives thereof,
  o-diaminobenzene and/or derivatives thereof,
  o-aminophenol derivatives, such as o-aminophenol,
  naphthaline derivatives having at least one hydroxy group,
  di- or trihydroxybenzene and/or derivatives thereof,
  pyridine derivatives,
  pyrimidine derivatives,
  monohydroxy indol derivatives and/or monoamino indol derivatives,
  monohydroxy indolin derivatives and/or monoamino indolin derivatives,
  pyrazolone derivatives, such as 1-phenyl-3-methylpyrazol-5-one,
  morpholine derivatives, such as 6-hydroxybenzomorpholine or 6-aminobenzomorpholine,
  quinoxaline derivatives, such as 6-methyl-1,2,3,4-tetrahydroquinoxaline.

Mixtures of two or more compounds from one or more of these classes are also included by the invention within the scope of this embodiment.

A further preferred embodiment is an agent according to the invention which is characterized in that it additionally includes one or more oxidation dye precursor products of the coupler type from the group formed from 3-aminophenol, 5-amino-2-methylphenol, 3-amino-2-chloro-6-methylphenol, 2-hydroxy-4-aminophenoxy ethanol, 5-amino-4-chloro-2-methylphenol, 5-(2-hydroxyethyl)-amino-2-methyl phenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino) ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dhydroxynaphthaline, 2, 7-dihydroxynaphthaline, 1,7-dihydroxynaphthaline, 1,8-dihydroxynaphthaline, 4-hydroxyindol, 6-hydroxyindol, 7-hydroxyindol, 4-hydroxyindolin, 6-hydroxyindolin, 7-hydroxyindolin and/or the physiologically acceptable salts thereof.

In a further very particularly preferred embodiment, an agent according to the invention is characterized in that it includes:
(A) as oxidation dye precursor product of the developer type, at least one compound of formula (I) from the group of
  1-N-methyl-2-[2-(pyrrolidin-1-yl)ethyl]benzene-1,4-diamine,
  1-N-methyl-2-[2-(piperidin-1-yl)ethyl]benzene-1,4-diamine,
  1-N-methyl-2-[2-(morpholin-4-yl)ethyl]benzene-1,4-diamine,
  2-[2-(pyrrolidin-1-yl)ethyl]benzene-1,4-diamine,
  2-[2-(piperidin-1-yl)ethyl]benzene-1,4-diamine and
  2-[2-(morpholin-4-yl)ethyl]benzene-1,4-diamine,
  and
(B) as oxidation dye precursor product of the coupler type, at least one compound from the group of resorcinol, 2-methylresorcinol and 4-chlororesorcinol.

The coupler components are preferably used in an amount of from 0.0001 to 10% by weight, preferably 0.01 to 5.0% by weight, in each case in relation to the total weight of the agent.

In one embodiment the agents according to the invention can include a compound of formula (I) as sole oxidation dye precursor product of the developer type. Depending on which shade is desired, however, a person skilled in the art can also use, in the agent according to the invention, other oxidation dye precursor products of the developer type which are different from the compounds of formula (I).

Preferred developer components are selected from p-phenylenediamine, p-toluenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diamino-propan-2-ol, bis-(2-hydroxy-5-aminophenyl)methane, 1,3-bis-(2,5-diaminophenoxy)-propan-2-ol, N,N'-bis-(4-aminophenyl)-1,4-diazacycloheptane, 1,10-bis-(2,5-diaminophenyl)-1,4,7,10-tetraoxadecane, 4-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, and the physiologically acceptable salts of these compounds, Particularly preferred additional developer components are p-toluenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine and/or 4,5-diamino-1-(2-hydroxyethyl)-pyrazole and the physiologically acceptable salts thereof In a further particularly preferred embodiment an agent according to the invention is therefore characterized in that it additionally includes
  one or more oxidation dye precursor products from the group formed from p-phenylenediamine, p-toluenediamine, 2-(2-hydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, bis-(2-hydroxy-5-aminophenyl)methane, 4-aminophenol, 4-amino-3-ethylphenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine and/or the physiologically acceptable salts thereof.

The oxidation dye precursor products of the developer which are different from the compounds of formula (I) which can be used in addition can be used in a total amount of from 0.001 to 3.0% by weight, preferably from 0.025 to 1.5% by weight, more preferably from 0.05 to 1.0% by weight, and particularly preferably from 0.1 to 0.5% by weight, in relation to the total weight of the agent.

The agents according to the invention can also additionally include at least one substantive dye. These are dyes which are drawn directly onto the hair and which do not require an oxidative process to form the colors. Substantive dyes are usually nitrophenylenediamines, nitroaminophenols, azo dyes, anthraquinones, triarylmethane dyes, or indophenols.

The substantive dyes are each used preferably in an amount of from 0.001 to 20% by weight, in particular from 0.05 to 5% by weight, in each case in relation to the total preparation for use. The total amount of substantive dyes is preferably at most 3% by weight.

Substantive dyes can be divided into anionic, cationic and non-ionic substantive dyes, which are selected and used by a person skilled in the art in accordance with the requirements of the carrier base.

Preferred anionic substantive dyes are the compounds known under the international names or trade names Bromophenol blue, Tetrabromophenol blue, Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52.

Preferred cationic substantive dyes are Basic Blue 7, Basic Blue 26, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Yellow 87, Basic Orange 31 and Basic Red 51.

In particular, non-ionic nitro dyes and quinone dyes and neutral azo dyes are suitable as non-ionic substantive dyes. Preferred non-ionic substantive dyes are the compounds known under the international names or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and also 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]-benzoic acid ester, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-4-nitrophenol.

The agents according to the invention can also include dyes analogous to natural dyes, in addition to the compound(s) of formula (I). Compositions according to the invention which include precursors of dyes analogous to natural dyes are preferably used as air-oxidative coloring agents. In this embodiment said compositions are consequently not mixed with an additional oxidizing agent.

Substances that are particularly suitable as precursors of hair dyes analogous to natural hair dyes are derivatives of 5,6-dihydroxyindolin, in particular 5,6-dihydroxyindolin, N-methyl-5,6-dihydroxyindolin, N-ethyl-5,6-dihydroxyindolin, N-propyl-5,6-dihydroxyindolin, N-butyl-5,6-dihydroxyindolin and also 5,6-dihydroxyindolin-2-carboxylic acid, and further derivatives of 5,6-dihydroxyindol, in particular 5,6-dihydroxyindol, N-methyl-5,6-dihydroxyindol, N-ethyl-5,6-dihydroxyindol, N-propyl-5,6-dihydroxyindol, N-butyl-5,6-dihydroxyindol, 5, 6-dihydroxyindol-2-carboxylic acid, and physiologically acceptable salts of the above-mentioned compounds.

The dye precursors of dyes analogous to natural dyes are in each case preferably used in an amount of from 0.001 to 5% by weight, in relation to the total preparation for use.

In the case of the oxidative coloring, the color can develop in principle with atmospheric oxygen. However, a chemical oxidizing agent is preferably also used, particularly when, in addition to the coloring, a lightening effect on human hair is also desired. This lightening effect can be desired independently of the coloring method. Persulfates, peroxodisulfates, chlorites, hypochlorites, and in particular hydrogen peroxide and/or one of the solid addition products thereof with organic or inorganic compounds are potential oxidizing agents.

In a further preferred embodiment an agent according to the invention is therefore characterized in that it additionally includes hydrogen peroxide as oxidizing agent.

In order to prevent a premature, undesired reaction of the oxidation dye precursor products by means of the oxidizing agent, oxidation dye precursor products and oxidizing agent itself are expediently packaged separately from one another and are only brought into contact just before use.

Products are preferred which include the agents according to the invention, therefore packaged as a multi-component packaging unit (kit-of-parts), including C1: a first component which is an agent according to the invention which includes at least one compound of formula (I), and C2: a second component, which is an oxidizing agent preparation.

C1 and C2 are mixed together shortly before use and thus form the ready-to-use dye.

The agents (C1) and (C2) can be mixed with one another for example in a mixing ratio of from 1:4 to 4:1. Mixing ratios of from 1:2 to 2:1 are particularly conventional, wherein the mixing ratios relate in each case to the ratio of the amounts by weight of (C1) and (C2) (for example 200 g of the agent (C1) can be mixed with 100 g of the agent (C2), giving a mixing ratio of 2:1).

The oxidizing agent preparation (C2) preferably includes, as oxidizing agent, hydrogen peroxide and/or one of the solid addition products thereof with organic or inorganic compounds, such as urea, melamine and sodium borate.

The amount of oxidizing agent in the ready-to-use agent is preferably 0.5 to 12% by weight, preferably 2 to 10% by weight, particularly preferably 3 to 6% by weight (calculated as 100% $H_2O_2$), in each case in relation to the ready-to-use agent.

Such oxidizing agent preparations are preferably aqueous, flowable oxidizing agent preparations. Here, preferred preparations are characterized in that the flowable oxidizing agent preparation—in relation to its weight—includes 40 to 90% by weight, preferably 50 to 85% by weight, particularly preferably 55 to 80% by weight, more preferably 60 to 77.5% by weight, and in particular 65 to 75% by weight of water.

In accordance with the invention, however, the oxidation dye can also be applied to the hair together with a catalyst, which activates the oxidation of the dye precursor products. Such catalysts are, for example, specific enzymes, iodides, quinones, or metal ions.

Just before use, the agent according to the invention (corresponding to the coloring preparation (C1)) is mixed with an oxidizing preparation (C2). The ready-to-use oxidative dye is obtained in this way.

For a sufficient swelling of the keratin fibers, the ready-to-use oxidative dye is preferably set to an alkaline pH value. The dyeing processes on keratin fibers also usually take place in alkaline medium. In order to protect the keratin fibers and also the skin to the greatest possible extent, however, the setting of an excessively high pH value is undesirable. It is therefore preferred when the pH value of the ready-to-use agent lies at a value of from 8.0 to 10.5, more preferably from 8.7 to 10.3, even more preferably from 9.0 to 10.2, and particularly preferably from 9.2 to 10.1. The specified pH values are values which were measured at a temperature of 22° C. using a glass electrode.

The alkalizing agents usable in accordance with the invention to set the preferred pH value can be selected from the group formed of ammonia, alkanolamines, basic amino acids, and inorganic alkalizing agents, such as alkaline (earth) metal hydroxides, alkaline (earth) metal silicates, alkaline (earth) metal phosphates, and alkaline (earth) metal hydrogen phosphates. Preferred inorganic alkalizing agents are sodium hydroxide, potassium hydroxide, sodium silicate, and sodium metasilicate. Organic alkalizing agents usable in accordance with the invention are preferably selected from monoethanolamine, 2-amino-2-methylpropanol, and triethanolamine. The basic amino acids usable as alkalizing agents according to the invention are preferably selected from the group formed from arginine, lysine, ornithine, and histidine, particularly preferably arginine. However, it has been found within the scope of the investigations for the present invention that agents which are preferred in accordance with the invention are also characterized in that they additionally include an organic alkalizing agent. One embodiment of the first subject matter of the invention is characterized in that the agent additionally includes at least one alkalizing agent which is selected from the group formed from ammonia, alkanolamines, and basic amino acids, in particular from ammonia, monoethanolamine, and arginine or acceptable salts thereof. The alkalizing agent(s) is/are preferably packaged together with the oxidation dye precursor products in the coloring preparation (C1).

In order to further increase the lightening, at least one $SiO_2$ compound, such as silicic acid or silicates, in particular water glasses, can be added additionally to the coloring preparation (C1) and/or the oxidizing agent preparation (C2). The $SiO_2$ compound can be included here in the coloring preparation (C1) and/or the oxidizing agent preparation (C2). In accordance with the invention, it can be preferred to use the $SiO_2$ compounds in quantities of from 0.05% by weight to 15% by weight, particularly preferably in amounts from 0.15% by weight to 10% by weight, and very particularly preferably in amounts from 0.2% by weight to 5% by weight, in each case in relation to the total weight of the coloring preparation (C1) or the total weight of the oxidizing agent preparation (C2). The specified amounts in each case reflect here the content of the $SiO_2$ compounds (without the water content thereof) in the agents.

The oxidative agent for changing the color (i.e. the coloring preparation (C1) and/or the oxidizing agent preparation (C2)) can also include additional active substances, auxiliaries and additives in order to improve the coloring or lightening performance and in order to set further desired properties of the agents.

The ready-to-use coloring agents are preferably provided as liquid preparation, and a further surface-active substance is therefore additionally added to the agents as necessary, wherein such surface-active substances are referred to as surfactants or as emulsifiers depending on the field of application: They are preferably selected from anionic, zwitterionic, amphoteric, and non-ionic surfactants and emulsifiers.

Agents suitable in accordance with the invention are characterized in that the agent additionally includes at least one anionic surfactant. Preferred anionic surfactants are fatty acids, alkyl sulfates, alkyl ether sulfates, and ether carboxylic acids having 10 to 20 C atoms in the alkyl group and up to 16 glycol ether groups in the molecule.

Agents suitable in accordance with the invention are characterized in that the agent additionally includes at least one zwitterionic surfactant. Preferred zwitterionic surfactants are betaines, N-alkyl-N,N-dimethylammonium glycinates, N-acylaminopropyl-N,N-dimethylammonium glycinates, and 2-alkyl-3-carboxymethyl-3-hydroxyethyl-imidazolines. A preferred zwitterionic surfactant is known under the INCI name Cocoamidopropyl Betaine.

Agents suitable in accordance with the invention are characterized in that the agent additionally includes at least one amphoteric surfactant. Preferred amphoteric surfactants are N-alkyl glycines, N-alkyl propionic acids, N-alkyl amino butyric acids, N-alkyl imino dipropionic acids, N-hydroxyethyl-N-alkyl amido propyl glycines, N-alkyl taurines, N-alkyl sarcosines, 2-alkylamino propionic acids, and alkyl amino acetic acids. Particularly preferred amphoteric surfactants are N-coco alkyl amino proprionate, coco acyl amino ethyl amino proprionate, and $C_{12}$-$C_{18}$-acyl sarcosine.

It has also proven to be advantageous when the agents include further non-ionogenic surfactants. Preferred non-ionic surfactants are alkyl polyglycosides and alkylene oxide addition products with fatty alcohols and fatty acids, in each case having 2 to 30 mol ethylene oxide per mol fatty alcohol or fatty acid. Preparations that have excellent properties are also obtained when they include fatty acid esters of ethoxylated glycerol as non-ionic surfactants.

The non-ionic, zwitterionic or amphoteric surfactants are used in proportions of from 0.1 to 45% by weight, preferably 1 to 30% by weight, and very particularly preferably from 1 to 15% by weight, in relation to the total amount of ready-to-use agents.

The ready-to-use agents for changing the color can also include at least one thickening agent. With regard to these thickening agents, there are no limitations in principle. Both organic and purely inorganic thickening agents can be used.

Suitable thickening agents are anionic, synthetic polymers, cationic, synthetic polymers, naturally occurring thickening agents, such as non-ionic guar gum, scleroglucan gum, or xanthan gum. gum arabic, ghatti gum, karaya gum, tragacanth gum, carrageenan gum, agar agar, locust bean gum, pectins, alginates, starch fractions, and derivatives such as amylose, amylopectin and dextrins and also cellulose derivatives, such as methyl cellulose, carboxy alkyl celluloses and hydroxyl alkyl cellulose, non-ionic, fully synthetic polymers, such as polyvinyl alcohol or polyvinyl pyrrolidone; and inorganic thickening agents, in particular sheet silicates, such as bentonite, particularly smectites, such as montmorillonite or hectorite.

It has also proven to be advantageous when the coloring agents, in particular when they additionally include hydrogen peroxide, include at least one stabilizer or complexing agent. Particularly preferred stabilizers are phenacetin, alkali benzoates (sodium benzoate) and salicylic acid. All complexing agents of the prior art can also be used. Complexing agents which are preferred in accordance with the invention are nitrogen-containing polycarboxylic acids, in particular EDTA and EDDS, and phosphonates, in particular 1-hydroxyethane-1-1-diphosphonate (HEDP) and/or ethylenediamine tetramethylene phosphonate (EDTMP) and/or diethylene triamine pentamethylene phosphonate (DTPMP) or sodium salts thereof.

Furthermore, the agents according to the invention can include further active substances, auxiliaries and additives, such as non-ionic polymers, such as vinylpyrrolidinone/vinylacrylate copolymers, polyvinylpyrrolidinone, vinylpyrrolidinone/vinylacetate copolymers, polyethylene glycols and polysiloxanes; additional silicones such as volatile or non-volatile, straight-chain, branched or cyclic, cross-linked or uncross-linked polyalkyl siloxanes (such as dimethicones or cyclomethicones), polyaryl siloxanes and/or polyalkyl aryl siloxanes, in particular polysiloxanes with organofunctional groups, such as substituted or unsubstituted amines (amodimethicones), carboxyl, alkoxy and/or hydroxyl groups (dimethicone copolyols), linear polysiloxane(A)-polyoxyalkylene(B) block copolymers, grafted silicone polymers; cationic polymers such as quaternized cellulose ethers, polysiloxanes having quaternary groups, dimethyldiallyl ammonium chloride polymers, acrylamide-dimethyldiallyl ammonium chloride copolymers, dimethylaminoethyl methacrylate-vinylpyrrolidinone copolymers quaternized with diethyl sulfate, vinylpyrrolidinone-imidazolinium-methochloride copolymers and quaternized polyvinyl alcohol; zwitterionic and amphoteric polymers; anionic polymers such as polyacrylic acids or cross-linked polyacrylic acids; structuring agents such as glucose, maleic acid and lactic acid, hair-conditioning compounds such as phospholipids, for example lecithin and cephalins; perfume oils, dimethyl isosorbide and cyclodextrins; fiber structure-improving active substances, in particular mono-, di- and oligosaccharides such as glucose, galactose, fructose, fruit sugars and lactose; dyes for coloring the agent; anti-dandruff active agents such as piroctone olamine, zinc omadine and climbazole; amino acids and oligopeptides; protein hydrolyzates of animal and/or plant origin as well as those in the form of their fatty acid condensation products or optionally anionically or cationically modified derivatives thereof; vegetable oils; light stabilizers and UV blockers; active agents such as panthenol, pantothenic acid, pantolactone, allantoin, pyrrolidinone carboxylic acids and salts thereof as well as bisabolol; polyphenols, in particular hydroxycinnamic acids, 6,7-dihydroxycoumarins, hydroxybenzoic acids, catechins, tannins, leukoanthocyanidins, anthocyanidins, flavanones, flavones and flavonols; ceramides or pseudoceramides; vitamins, provitamins and vitamin precursors; plant extracts; fats and waxes such as fatty alcohols, beeswax, montan wax and paraffins; swelling and penetrating substances such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate and PEG-3 distearate; pigments, as well as propellants such as propane-butane mixtures, $N_2O$, dimethyl ether, $CO_2$ and air.

These further substances will be selected by a person skilled in the art in accordance with the desired properties of the agents. With regard to further optional components and the used amounts of these components, reference is made expressly to the relevant handbooks known to a person skilled in the art. The additional active substances and auxiliaries are used in the agents according to the invention preferably in amounts of, in each case, 0.0001 to 25% by weight, in particular from 0.0005 to 15% by weight, in each case in relation to the total weight of the coloring preparation (C1) and/or the oxidizing agent preparation (C2).

Compounds of formula (I) are not previously known from the literature. A second subject of the present invention is therefore constituted by compounds of formula (I)

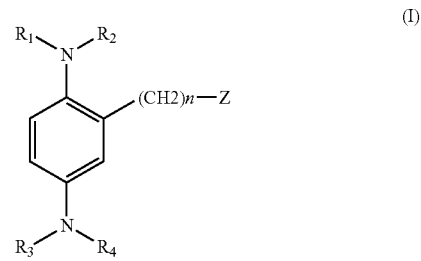

(I)

in which
R1, R2, R3, R4 independently of one another, stand for a hydrogen atom, a $C_1$-$C_6$ alkyl group, a $C_2$-$C_6$ alkenyl group, a hydroxy-($C_1$-$C_6$)-alkyl group, a polyhydroxy-($C_2$-$C_6$)-alkyl group or a $C_1$-$C_6$-alkoxy-$C_2$-$C_6$-alkyl group,
n stands for an integer from 2 to 6, and
Z stands for an aromatic or aliphatic heterocycle or for an aromatic or aliphatic carbocycle.

That said with regard to the agents according to the invention applies, mutatis mutandis, with regard to further preferred embodiments of these compounds.

EXAMPLES

The compounds according to the invention can be produced in accordance with the following schema:

Synthesis example 1 synthesis of 2-[2-(pyrrolidin-1-yl)ethyl]benzene-1,4-diamine, dihydrochloride 1.1. Synthesis of indolin-2-one

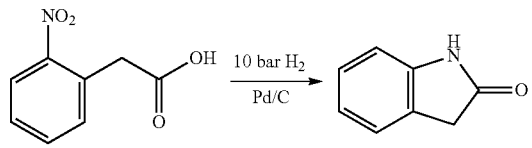 [SMILES: O=C(O)Cc1ccccc1[N+](=O)[O-] ; O=C1Cc2ccccc2N1]

1.0 g Pd (5% on carbon) was added to a solution of 2-nitrophenyl acetic acid (99.3 g, 0.539 mol) in 1800 mL ethanol and 200 mL water and was stirred at 10 bar $H_2$ in an autoclave for 24 h.

The catalyst was then filtered off, and the filtrate was evaporated until dry. The residue was recrystallized from 650 mL water and 18 mL ethanol. 1 Indolin-2-one in the form of light-beige crystals was obtained (63.1 g, 88%).

fp: 126.3-126.7° C.

$^1$HNMR (400 MHz, $d_6$-DMSO): δ=3.43 (s, 2H, $H_3$), 6.82 (d, 1H, $H_5$), 6.92 (t, 1H, $H_6$), 7.15 (m, 2H, $H_{5,7}$), 10.40 (bs, 1H, NH)

$^{13}$CNMR (100 MHz, $d_6$-DMSO): δ=36.1 ($C_3$), 109.5 ($C_7$), 121.5 ($C_5$), 124.7 ($C_4$), 126.1 ($C_9$), 127.8 ($C_6$), 144.0 ($C_8$), 176.8 ($C_2$)

1.2. Synthesis of 5-nitroindolin-2-one

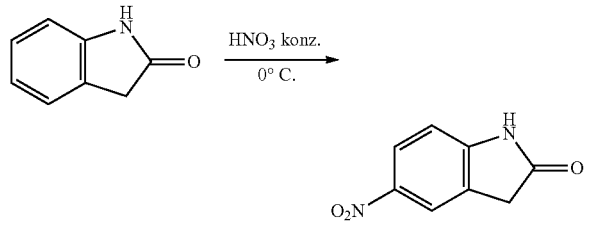

Concentrated nitric acid (9.31 g, 0.096 mol) was added in drops over 60 min and at 0° C. to a solution of indolin-2-one (13.3 g, 0.100 mol) in concentrated sulfuric acid (67 mL), and the resultant dark-brown solution was then stirred at this temperature for 1 h.

The reaction mixture was then poured over ice and sucked away. The residue was washed again with water and dried, then recrystallized from isopropanol. 5-nitroindolin-2-one in the form of golden, shiny sheets was obtained (12.28 g, 69%).

fp: >300° C.

$^1$HNMR (300 MHz, $d_6$-DMSO): δ=3.61 (s, 2H, $H_2$), 6.97 (d, 1H, $H_7$), 8.05 (d, 1H, $H_6$), 8.05 (s, 1H, $H_4$), 8.15 (d, 1H, $H_6$), 11.03 (bs, 1H, NH).

$^{13}$C NMR (100 MHz, DMSO): 35.9 ($C_2$), 109.2 ($C_7$), 120.3 ($C_4$), 125.1 ($C_6$), 127.2 ($C_9$), 142.0 ($C_5$), 150.6 ($C_8$), 177.0 ($C_2$)

1.3. Synthesis of tert-butyl 5-nitro-2-oxo-indolin-1-carboxylate

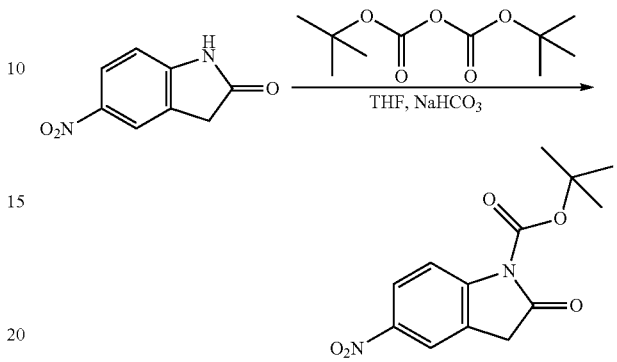

Di-tert-butyl dicarbonate (54.6 g, 0.25 mol) and sodium hydrogen carbonate (75.6 g, 0.90 mol) were added to a solution of 5-nitroindolin-2-one (17.8 g, 0.10 mol) in 1500 mL THF at room temperature in a nitrogen atmosphere and were stirred for 67 h. The mixture was then stirred for a further 50 h at 50° C., and the reaction solution was then filtered. The filtrate was evaporated until dry, and water was rubbed into the residue, which was then sucked away again and rinsed again with water. After the drying in a vacuum, tert-butyl 5-nitro-2-oxo-indolin-1-carboxylate in the form of a light-brown powder was obtained (20.8 g, 75%).

$^1$HNMR (300 MHz, $d_6$-DMSO): δ=1.61 (s, 9H, tBu), 3.87 (s, 2H, $H_2$), 7.89 (d, 1H, $H_7$), 8.20 (s, 1H, $H_4$), 8.25 (d, 1H, $H_6$).

$^{13}$C NMR (100 MHz, DMSO): 28.0 ($CH_3$), 36.3 ($C_2$), 84.8 ($C(CH_3)$), 114.9 ($C_7$), 120.1 ($C_4$), 124.4 ($C_6$), 126.5 ($C_9$), 143.8 ($C_5$), 146.6 ($C_8$), 148.8 (C=O), 177.0 ($C_2$).

1.4 Synthesis of tert-butyl N-[2-(2-hydroxyethyl)-4-nitrophenyl]carbamate

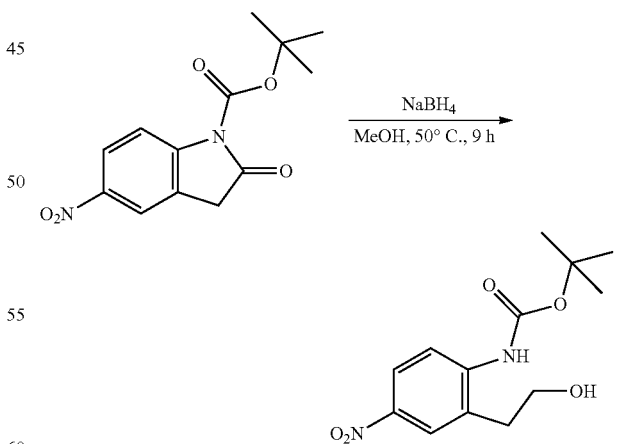

Sodium borohydride was added in batches over 30 min (1.89 g, 0.25 mol) (75.6 g, 0.90 mol) to a solution of tert-butyl 5-nitro-2-oxo-indolin-1-carboxylate (5.56 g, 0.02 mol) in 150 mL methanol at room temperature in a nitrogen atmosphere. The temperature rose steadily during this process to 40° C., and the mixture was then stirred for 9 h at 50°

C. The reaction mixture was then diluted with 500 mL water and extracted 5 times, in each case with 200 mL tBME. The combined ether extracts were then dried over sodium sulfate, filtered, and evaporated until dry. The residue was recrystallized from 150 mL water and 83 mL ethanol. Tert-butyl N-[2-(2-hydroxyethyl)-4-nitro-phenyl] carbamate in the form of a light-brown powder was obtained (3.4 g, 60%).

fp: 108.9-110.7° C.

$^1$HNMR (300 MHz, $d_6$-DMSO): δ=1.50 (s, 9H, tBu), 2.89 (dd, 2H, $H_{1'}$), 3.72 (m, 2H, $H_{2'}$), 4.85 (br s, OH), 7.93 (d, 1H, $H_6$), 8.10 (dd, 1H, $H_5$), 8.13 (s, 1H, $H_3$), 9.34 (1H, NH).

$^{13}$C NMR (100 MHz, DMSO): 28.3 (CH$_3$), 34.6 ($C_{1'}$), 61.6 ($C_{2'}$), 80.5 (C(CH$_3$)), 121.9 ($C_6$), 122.6 ($C_5$), 126.1 ($C_3$), 132.8 ($C_2$), 142.7 ($C_4$), 144.4 ($C_1$), 153.0 (C=O).

1.5. Synthesis of 2-[2-(tert-butoxycarbonylamino)-5-nitro-phenyl]ethyl methane sulfonate

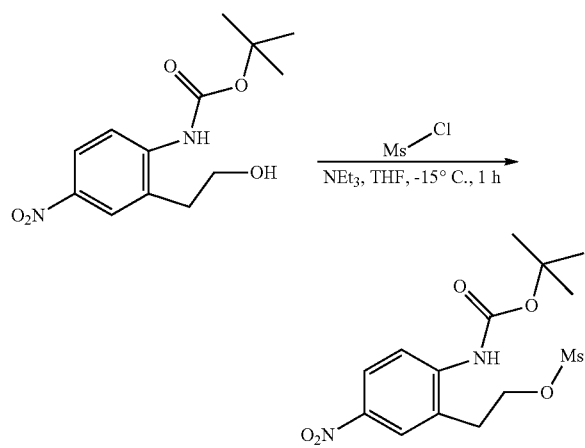

A solution of methane sulfonyl chloride (20.7 g, 0.18 mol) in 160 mL THF was added in drops over 50 min at −15° C. in a nitrogen atmosphere to a suspension of tert-butyl N-[2-(2-hydroxyethyl)-4-nitro-phenyl]carbamate (25.4 g, 0.09 mol) and triethylamine (26.3 g, 0.26 mol) in 360 mL THF, and the mixture was then stirred for 30 min at room temperature.

By adding 1450 mL of a 15% ammonium chloride solution, the pH was set to 7 and the organic phase was separated off. This was dried over sodium sulfate, filtered, and evaporated. The residue was first recrystallized from 250 mL isopropanol and then from 100 mL water and 250 mL ethanol.

2-[2-(tert-butoxycarbonylamino)-5-nitro-phenyl]ethyl methane sulfonate in the form of beige crystals was obtained (18.0 g, 55%)

fp: 128° C. (decomp.)

$^1$HNMR (300 MHz, $d_6$-DMSO): δ=1.50 (s, 9H, tBu), 3.12 (s, 3H, Me), 3.19 (dd, 2H, $H_{1'}$), 4.43 (t, 2H, $H_{2'}$), 7.83 (d, 1H, $H_6$), 8.12 (dd, 1H, $H_5$), 8.19 (s, 1H, $H_3$), 9.20 (1H, NH). $^{13}$C NMR (100 MHz, DMSO): 28.4 (C(CH$_3$)), 30.0 ($C_{1'}$), 37.0 (Me), 69.2 ($C_{2'}$), 80.6 (C(CH$_3$)), 123.1 ($C_6$), 124.0 ($C_5$), 125.9 ($C_3$), 130.1 ($C_2$), 143.2 ($C_4$), 143.9 ($C_1$), 153.4 (C=O).

1.6. Synthesis of 2-[2-(diacetylamino)-5-nitro-phenyl]ethyl methane sulfonate

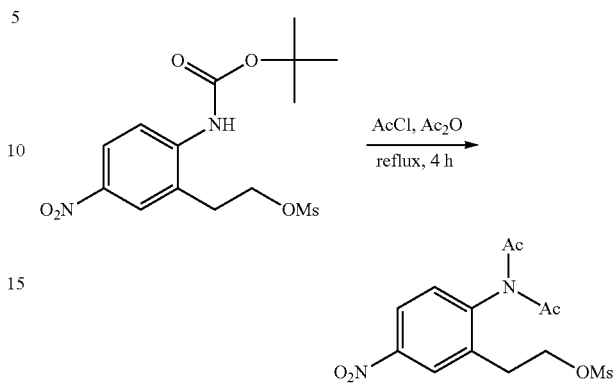

2-[2-(tert-butoxycarbonylamino)-5-nitro-phenyl]ethyl methane sulfonate (4.00 g) was suspended with acetyl chloride (46.17 g, 1.7 mol) and heated. This resulted in a solution, which was boiled to reflux over 3 h and evaporated until dry. The red-brown residue was recrystallized from 32.8 g toluene.

The obtained precipitate (0.45 g) was placed in acetic anhydride (11.25 g, 0.110 mol), boiled for 2 h at 80° C., and evaporated until dry. The oil obtained here crystallized out after a few days. By smashing against an earthenware slab, 2-[2-(diacetylamino)-5-nitro-phenyl]ethyl methane sulfonate in the form of light orange crystals was obtained (0.26 g, 6.8%).

1.7. Synthesis of N-acetyl-N-[4-nitro-2-(2-pyrrolidin-1-ylethyl)phenyl]acetamide

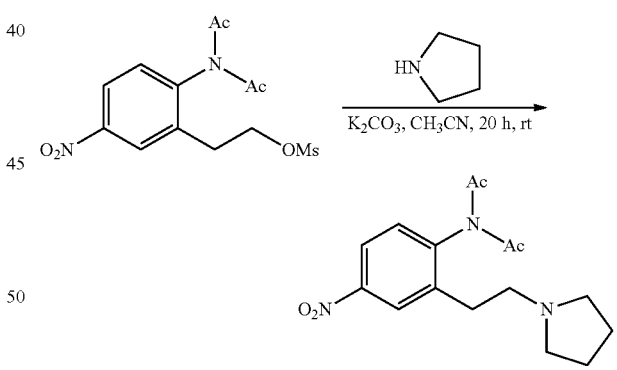

A mixture of 2-[2-(diacetylamino)-5-nitro-phenyl]ethyl methane sulfonate (1.30 g), pyrrolidine (0.46 g) and potassium carbonate (1.30 g) was stirred in 30 mL acetonitrile for 12 hours at room temperature. 50 mL of a saturated aqueous sodium hydrogen carbonate solution were then added. The resultant mixture was evaporated in a vacuum. The residue was then extracted with acetic acid ethyl ester, and the combined organic phases were dried with sodium sulfate, filtered, and then evaporated until dry.

N-acetyl-N-[4-nitro-2-(2-pyrrolidin-1-ylethyl)phenyl]acetamide in the form of an oily solid was obtained (0.75 g, 62%).

1.8 Synthesis of 2-[2-(pyrrolidin-1-yl)ethyl]benzene-1,4-diamine, dihydrochloride

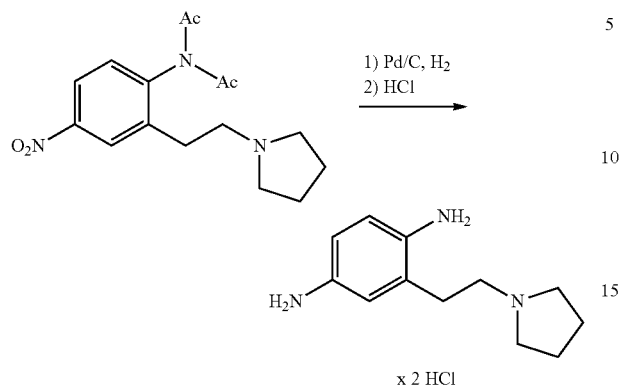

Step 1: Hydrogenation in the shaking vessel:
5% by weight of palladium on carbon was added to a solution of 0.75 g N-acetyl-N-[4-nitro-2-(2-pyrrolidin-1-ylethyl)phenyl]acetamide in 400 mL ethanol, and the mixture was shaken for 21 h at room temperature.

Step 2: Cleaving of the protective group (similarly to Guilhemat, Robert; Pereyre, Michel; Petraud, Michel, *Bulletin de la Societe Chimique de France* [French Journal of Chemistry], 1980, 2 (7-8), 334-344.

Once the reaction was complete, the reaction solution was poured over 8 mL of hydrochloric acid (conc.), filtered off from the catalyst, and heated for 3 h under reflux and evaporated until dry. Ethanol was added to the residue, which was evaporated again. The resultant precipitate was sucked away and rinsed again with a little ice-cold ethanol.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An agent for oxidatively changing the color of keratinic fibers, in particular human hair, including, in a cosmetic carrier, at least one oxidation dye precursor product of formula (I) and/or physiologically acceptable salt thereof,

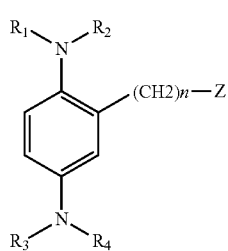
(I)

in which

R1, R2, R3, R4 independently of one another, stand for a hydrogen atom, a $C_1$-$C_6$ alkyl group, a $C_2$-$C_6$ alkenyl group, a hydroxy-($C_1$-$C_6$)-alkyl group, a polyhydroxy-($C_2$-$C_6$)-alkyl group, or a $C_1$-$C_6$-alkoxy-$C_2$-$C_6$-alkyl group, n stands for an integer from 3 to 6, and Z stands for an aromatic or aliphatic heterocycle or for an aromatic or aliphatic carbocycle.

2. The agent according to claim 1, wherein
R1, R2, R3, R4 independently of one another, stand for a hydrogen atom, a $C_1$-$C_6$-alkyl group or a 2-(hydroxy)ethyl group.

3. The agent according to claim 1, wherein
one of the groups from R1, R2, R3 and R4 stands for a $C_1$-$C_6$ alkyl group, and the other three groups from R1, R2, R3 and R4 stand for a hydrogen atom.

4. The agent according to claim 1, wherein
R3, R4 both stand for a hydrogen atom.

5. The agent according to claim 1, wherein
R1 stands for a methyl group or for a hydrogen atom, and R2 stands for a hydrogen atom.

6. The agent according to claim 1, wherein
Z stands for an aromatic or aliphatic heterocycle of formulas (II) to (X),

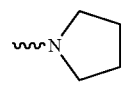
(II)

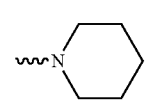
(III)

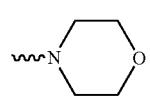
(IV)

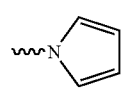
(V)

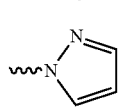
(VI)

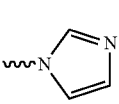
(VII)

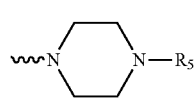
(VIII)

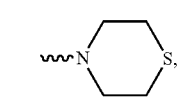
(IX)

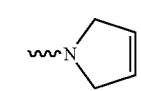
(X)

wherein
R5 stands for a hydrogen atom, a $C_1$-$C_6$ alkyl group or a $C_2$-$C_6$ alkenyl group.

7. The agent according to claim 6, wherein
Z stands for an aromatic or aliphatic heterocycle of formula (II), (III), (IV) or (V).

8. The agent according to claim 1, wherein
Z stands for an aromatic or aliphatic carbocycle of formulas (XI) to (XIII),

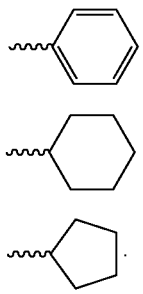

(XI)

(XII)

(XIII)

9. The agent according to claim 1, wherein the at least one oxidation dye precursor product of formula (I) is selected from the group consisting of 1-N-methyl-2-[3-(pyrrolidin-1-yl)propyl]benzene-1,4-diamine

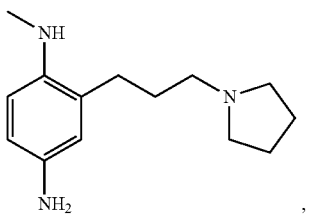 [SMILES: CNc1ccc(N)cc1CCCN1CCCC1]

1-N-methyl-2-[3-(piperidin-1-yl)propyl]benzene-1,4-diamine

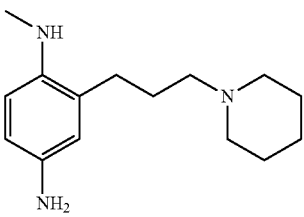

1-N-methyl-2-[3-(morpholin-4-yl)propyl]benzene-1,4-diamine

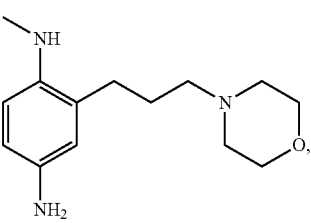 [SMILES: CNc1ccc(N)cc1CCCN1CCOCC1]

1-N-methyl-2-[3-(1H-pyrrol-1-yl)propyl]benzene-1,4-diamine

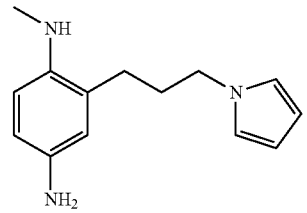

1-N-methyl-2-[3-(1H-pyrazol-1-yl)propyl]benzene-1,4-diamine

1-N-methyl-2-[3-(1H-imidazol-1-yl)propyl]benzene-1,4-diamine

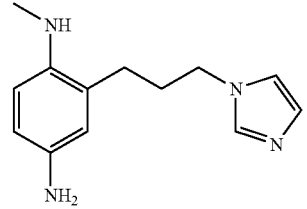

1-N-methyl-2-[3-(piperazin-1-yl)propyl]benzene-1,4-diamine

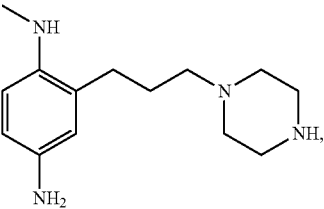 [SMILES: CNc1ccc(N)cc1CCCN1CCNCC1]

1-N-methyl-2-[3-(4-methylpiperazin-1-yl)propyl]benzene-1,4-diamine

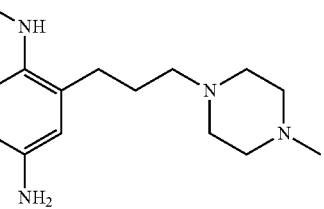

1-N-methyl-2-[3-(thiomorpholin-4-yl)propyl]benzene-1,4-diamine

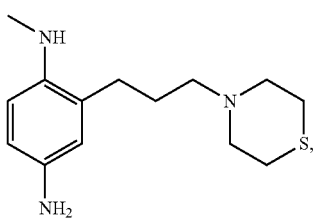 [SMILES: CNc1ccc(N)cc1CCCN1CCSCC1]
1-N-methyl-2-[3-(2,5-dihydro-1H-pyrrol-1-yl)propyl]
benzene-1,4-diamine
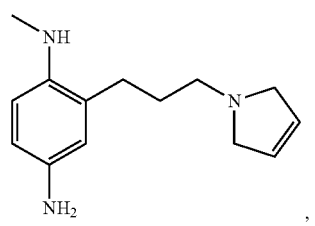 [SMILES: CNc1ccc(N)cc1CCCN1CC=CC1]
2-[3-(pyrrolidin-1-yl)propyl]benzene-1,4-diamine
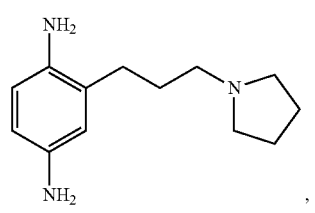 [SMILES: Nc1ccc(N)c(CCCN2CCCC2)c1]
2-[3-(piperidin-1-yl)propyl]benzene-1,4-diamine
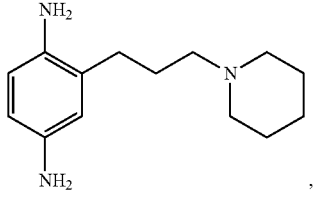 [SMILES: Nc1ccc(N)c(CCCN2CCCCC2)c1]
2-[3-(morpholin-4-yl)propyl]benzene-1,4-diamine
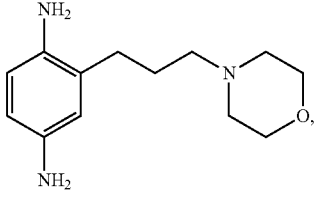
2-[3-(1H-pyrrol-1-yl)propyl]benzene-1,4-diamine
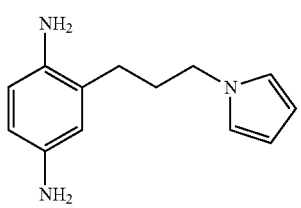
2-[3-(1H-pyrazol-1-yl)propyl]benzene-1,4-diamine
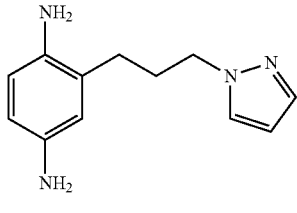
2-[3-(1H-imidazol-1-yl)propyl]benzene-1,4-diamine
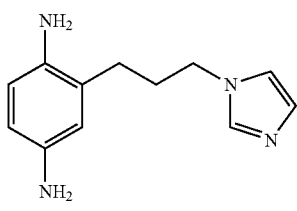
2-[3-(piperazin-1-yl)propyl]benzene-1,4-diamine
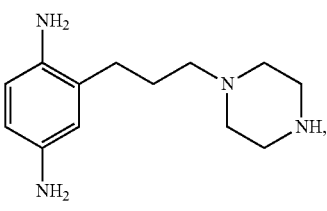
2-[3-(4-methylpiperazin-1-yl)propyl]benzene-1,4-diamine
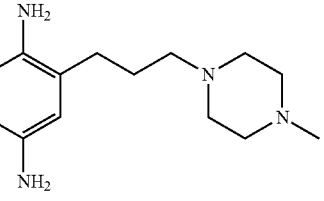

2-[3-(thiomorpholin-4-yl)propyl]benzene-1,4-diamine

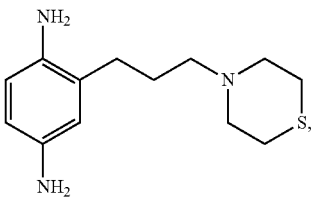 [SMILES: Nc1ccc(N)c(CCCN2CCOCC2)c1]

2-[3-(2,5-dihydro-1H-pyrrol-1-yl)propyl]benzene-1,4-diamine

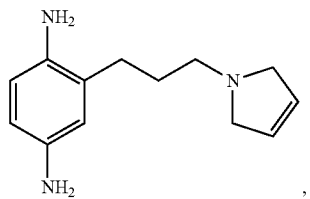 [SMILES: Nc1ccc(N)c(CCCN2CC=CC2)c1]

and the physiologically acceptable salts of these compounds.

10. The agent according to claim 1, wherein the one or more oxidation dye precursor products of formula (I) is/are included in a total amount of from 0.001 to 5.0% by weight, in relation to the total weight of the agent.

11. The agent according to claim 1, further including one or more oxidation dye precursor products selected from the group consisting of 3-aminophenol, 5-amino-2-methylphenol, 3-amino-2-chloro-6-methylphenol, 2-hydroxy-4-aminophenoxy ethanol, 5-amino-4-chloro-2-methylphenol, 5-(2-hydroxyethyl)-amino-2-methyl phenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dhydroxynaphthaline, 2,7-dihydroxynaphthaline, 1,7-dihydroxynaphthaline, 1,8-dihydroxynaphthaline, 4-hydroxyindol, 6-hydroxyindol, 7-hydroxyindol, 4-hydroxyindolin, 6-hydroxyindolin, 7-hydroxyindolin, and the physiologically acceptable salts thereof.

12. The agent according to claim 1, further including one or more oxidation dye precursor products selected from the group consisting of p-phenylenediamine, p-toluenediamine, 2-(2-hydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, bis-(2-hydroxy-5-aminophenyl)methane, 4-aminophenol, 4-amino-3-ethylphenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine and the physiologically acceptable salts thereof.

13. The agent according to claim 1, further including hydrogen peroxide as oxidizing agent.

14. A compound according to formula (I) as described in claim 1.

* * * * *